United States Patent [19]

Franceschi et al.

[11] 4,447,432
[45] May 8, 1984

[54] AZINO RIFAMYCINS

[75] Inventors: Giovanni Franceschi; Leonardo Marsili; Aurora Sanfilippo, all of Milan; Sergio Vioglio, Cusano Milanino, all of Italy

[73] Assignee: Farmitalia Carlo Erba S.P.A., Milan, Italy

[21] Appl. No.: 427,467

[22] Filed: Sep. 29, 1982

[30] Foreign Application Priority Data

Nov. 17, 1981 [GB] United Kingdom ................. 8134549

[51] Int. Cl.³ ................... A61K 31/395; C07D 498/08
[52] U.S. Cl. ........................ 424/248.54; 260/239.3 P; 424/267; 424/274; 424/244
[58] Field of Search .................................. 260/239.3 P; 424/248.54, 267, 274, 244

[56] References Cited

U.S. PATENT DOCUMENTS 4,327,096 4/1982 Marsili et al. ................. 260/239.3 P Primary Examiner—Robert T. Bond
Attorney, Agent, or Firm—Oblon, Fisher, Spivak, McClelland & Maier

[57] ABSTRACT

There are provided azino rifamycin compounds of the formula (I):

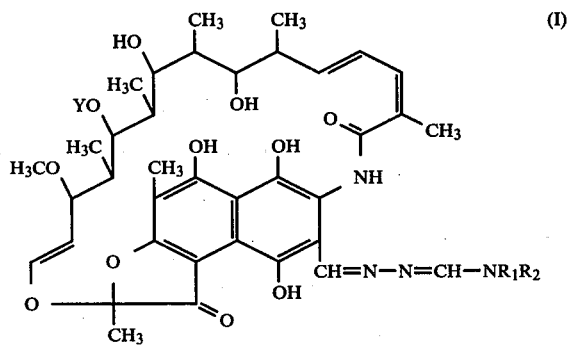

$Y=H$ or $CH_3CO$; $R_1$ linear or branched $C_1$-$C_7$ alkyl or $C_3$-$C_4$ alkenyl- $R_2$=linear or branched $C_1$-$C_7$ alkyl, $C_2$-$C_4$ chloroalkyl, $C_3$-$C_4$ alkenyl, Cycloalkyl having 3 to 7 C atoms in the ring, cycloalkyl alkyl having 3 to 6 C atoms in the ring, phenyl, or $C_7$-$C_8$ aralkyl, unsubstituted or mono-substituted by a halogen atom in the aryl group; or $NR_1R_2$=a cyclic moiety having 5 to 8 C atoms, unsubstituted or substituted by 1 or 2 $CH_3$ groups, morpholino.

The compounds inhibit the growth of gram positive bacteria and *Mycobacterium tuberculosis*.

Oxidized compounds, preparative methods and pharmaceutical compositions are also described and claimed.

5 Claims, No Drawings

AZINO RIFAMYCINS

DESCRIPTION

The invention relates to azino rifamycins, to methods for their preparation and to pharmaceutical compositions containing them.

The invention provides rifamycin compounds having the general formula (I)

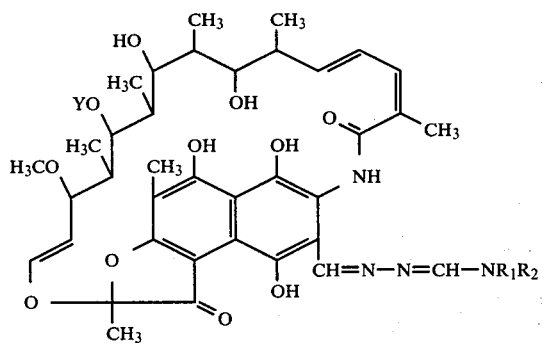

wherein Y represents a hydrogen atom or an acetyl group and either $R_1$ represents a linear or branched alkyl group having from 1 to 7 carbon atoms or an alkenyl group having 3 or 4 carbon atoms, and $R_2$ represents a linear or branched alkyl group having from 1 to 7 carbon atoms, a chloroalkyl group having from 2 to 4 carbon atoms, an alkenyl group having 3 or 4 carbon atoms, a cycloalkyl group having from 3 to 7 carbon atoms in the ring, a cycloalkyl alkyl group having from 3 to 6 carbon atoms in the ring, a phenyl group, an unsubstituted aralkyl group having 7 or 8 carbon atoms or an aralkyl group having 7 or 8 carbon atoms and substituted by one halogen atom in the aryl group, or $R_1$ and $R_2$ together with the nitrogen atom to which they are bonded represent an unsubstituted cyclic moiety having from 5 to 8 carbon atoms, a cyclic moiety having from 5 to 8 carbon atoms substituted by one or two methyl group(s), or a morpholino group or a 4-alkyl-1-piperazinyl group.

The invention also provides compounds of the general formula (II)

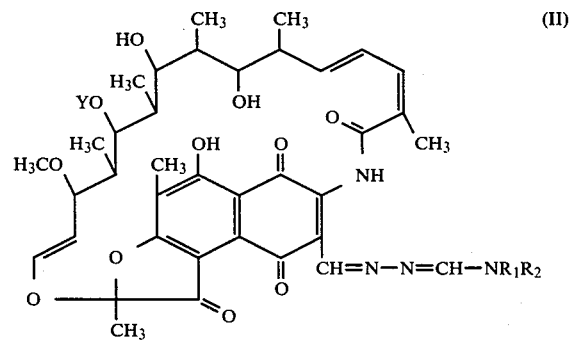

wherein Y, $R_1$ and $R_2$ are as above defined. These compounds of the general formula (II) are oxidation products of the compounds of the general formula (I).

The rifamycin compounds according to the invention have antibacterial activity against Gram-positive and Gram-negative bacteria and against *Mycobacterium Tuberculosis*. The compounds of the general formula I are orange to red solids, while those of the general formula II are violet or dark black solids. They are generally soluble in most organic solvents, such as chlorinated solvents, alcohols esters and aromatic hydrocarbons.

The compounds of the general formula I may be prepared by a process comprising reacting a 3-hydrazonomethyl-rifamycin SV of the general formula (III)

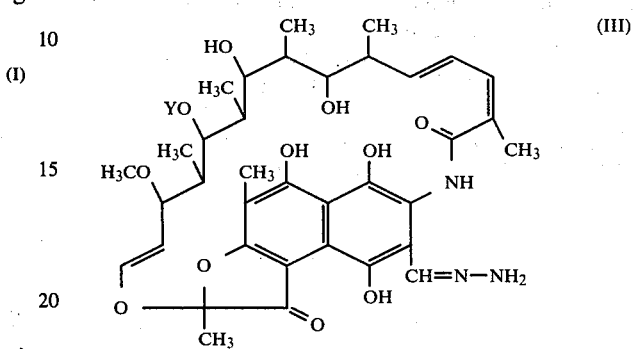

wherein Y represents a hydrogen atom or an acetyl group, in the presence of a tertiary amine and of an aprotic solvent, with a chloroformiminium chloride of the general formula (IV)

wherein $R_1$ and $R_2$ are as above defined. This process is within the scope of the invention.

The compounds of the general formula III are disclosed in U.S. Pat. No. 3,342,810.

The compounds of the general formula (IV) are described in British Patent Specification No. 1,293,590.

The tertiary amine is suitably triethylamine. Several aprotic solvents are suitable, including tetrahydrofuran, dioxan, chloroform, dichloromethane, 1,2-dichloroethane, benzene or toluene.

The compounds of the general formula (II) may be prepared from the corresponding compounds of the general formula (I) by oxidation with $MnO_2$, potassium ferricyanide or with other oxidating agents of common use in this art.

The rifamycin compounds according to the invention may be admixed with a pharmaceutically acceptable carrier or diluent to form a pharmaceutical composition within the scope of the invention. Whether alone or in such a composition, they may be formulated for administration in conventional unit dosage forms.

The invention is illustrated by the following Examples, in which the PMR spectra have been determined while using TMS as internal standard: the values of δ are p.p.m.

EXAMPLE 1

3-(N-piperidinomethyl-azino) methylrifamycin SV 5 g of 3-formyl-rifamycin SV was dissolved in 250 ml of tetrahydrofuran and dropped into a solution of 0.35 ml of hydrazine hydrate in 50 ml of tetrahydrofuran during 15 minutes under stirring and at −20° C. The absence of 3-formyl-rifamycin SV was checked by thin layer chromatography and 2 ml of triethylamine was added keeping the temperature at −20° C. 5 g of chloropiperidylformiminium chloride was added portionwise and the mixture was gently warmed to room temperature under stirring.

350 ml of ethyl acetate was added and the resulting solution was washed with water. After drying on anhydrous sodium sulphate the solvent was evaporated off and the crude product was crystallized from methanol and then from acetone.

2.3 g of a red compound of general formula I, wherein Y=COCH$_3$ and NR$_1$R$_2$=piperidyl, was obtained.

PMR (CDCl$_3$): −0.27 δ[d, CH$_3$ (34)]; 0.65 δ[d, CH$_3$(33)]; 0.75 δ[d, CH$_3$(31)]; 0.99 δ[d, CH$_3$ (32)]; 1.65 δ

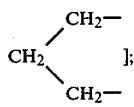

1.79 δ[s, CH$_3$(13)]; 2.06 δ[s, CH$_3$(36)]; 2.10 δ[s, CH$_3$(30)]; 2.23 δ[s, CH$_3$ (14)]; 3.04 δ[s, CH$_3$ (37)]; 7.73 and 9.03 δ[2 s, —CH=N—N=CH—N<]; 11.93 δ

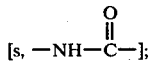

13.27 and 13.87 δ[s, OH—C(1), OH—C(8), OH—C(4)].
MS: 834 (M+)

The above compound was oxidized with MnO$_2$ in dichloromethane solution to give the corresponding quinone of formula (II).
MS: 832 (M+)
Rf: 0.37 in CH$_2$Cl$_2$:MeOH 20:1

The 3-(N-piperidinomethyl-azino)methylrifamycin SV was desacetylated according to Helv. Chim. Acta 56, 2335 (1973) to give the corresponding compound of formula (I) in which Y=H.
MS: 792 (M+)
Rf: 0.24 in CH$_2$Cl$_2$:MeOH 20:1

This last mentioned desacetyl derivative was oxidized with M$_n$O$_2$ in dichloromethane solution to give the corresponding quinone of formula (II)
MS: 790 (M+)
Rf: 0.22 in CH$_2$Cl$_2$: MeOH 20:1

EXAMPLE 2

3-(N-morpholinomethyl-azino)methylrifamycin SV

Following the procedure described in Example 1 and reacting 3-formyl-rifamycin SV with chloromorpholinoformiminium chloride a compound of formula I was obtained wherein Y=COCH$_3$ and NR$_1$R$_2$=morpholino.

PMR (CDCl$_3$): −0.28 δ[d, CH$_3$ (34)]; 0.65 δ[d, CH$_3$(33)]; 0.76 δ[d, CH$_3$(31)]; 0.99 δ[d, CH$_3$(32)]; 1.79 δ[s, CH$_3$(13)]; 2.06 δ[s, CH$_3$(36)]; 2.10 δ[s, CH$_3$(30)]; 2.23 δ[s, CH$_3$(14)]; 3.04

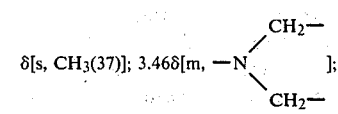

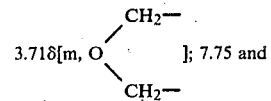
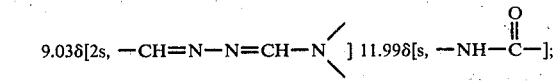

13.24, 13.69 and 13.83 δ[3s, OH—C(1), OH—C(4), OH—C(8)].
MS: 836 (M+)

EXAMPLE 3

3-(N-dimethylaminomethyl-azino)methylrifamycin SV

Following the procedure described in Example 1 and reacting 3-formyl-rifamycin SV with chlorodimethylformiminium chloride a compound of formula I was obtained wherein Y=COCH$_3$ and R$_1$=R$_2$=CH$_3$.

PMR(CDCl$_3$) —0.26 δ[d, CH$_3$(34)]; 0.68 δ[d, CH$_3$(33)]; 0.77 δ[d, CH$_3$ (31)]; 1.04 δ[d, CH$_3$ (32)]; 1.85 δ[s, CH$_3$(13)]; 2.10 δ[s, CH$_3$(36)]; 2.17 δ[s, CH$_3$(30)]; 2.27 δ[s, CH$_3$(14)]; 3.03 δ

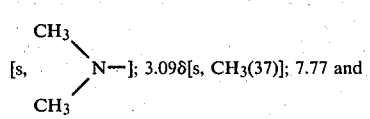

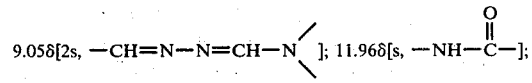

13.29 and 13.92 δ[OH—C(1), OH—C(8), OH—C(4)].
MS: 794 (M+)

EXAMPLE 4

3-(N-hezahydroazepinmethyl-azino)methylrifamycin SV 3 g of 3-formyl-rifamycin SV was dissolved in 50 ml of dichloroethane and dropped into a solution of 0.2 ml of hydrazine hydrate in 25 ml of dichloroethane during 15 minutes under stirring and at −20° C. After 15' the resulting solution of 3-hydrazonomethyl-rifamycin SV was allowed to reach +5° C., 1.2 ml of triethylamine and then 3 g of chlorohexahydrozepinylformiminium chloride was added. The mixture was stirred for 15 minutes then was diluted with 100 ml of dichloroethane and washed with water.

After drying on anhydrous sodium sulphate the solvent was evaporated off and the crude product was purified by column chromatography on silica gel, using ethyl acetate-methanol as eluents. The pure product thus obtained was crystallized from acetone.

0.70 g of a red compound of general formula I, wherein Y=COCH$_3$ and NR$_1$R$_2$=hexahydroazepinyl, was obtained.
MS: 848 (M+)

EXAMPLE 5

3-(N-morpholinomethyl-azino)methylrifamycin S 0.25 g of the compound obtained in example 2 was dissolved in 30 ml of chloroform and 0.20 g of manganese dioxide was added. A stream of air was bubbled through the suspension for 180 minutes, the manganese dioxide was filtered and the solvent was evaporated off. The residue was crystallized from methanol. 0.150 g of a violet compound was obtained.
MS: 834 (M+)

EXAMPLE 6

3-(N-di-n-propylaminomethyl-azino)methylrifamycin SV

A solution of 3 g of 3-formyl-rifamycin SV in tetrahydrofuran (150 ml) was added to 0.2 ml of hydrazine hydrate dissolved in tetrahydrofuran (50 ml) cooled at −20° C. After 15' the resulting solution of 3-hydrazonomethyl-rifamycin SV was allowed to reach 0° C., 1.2 ml of triethylamine and then 3 g of chloro-di-n-propylformiminium chloride were added.

After 15' at room temperature the reaction mixture was diluted with 200 ml of ethyl acetate, washed with 3% sodium bicarbonate aqueous solution and then with water. The organic phase was dried over anhydrous sodium sulphate, the solution was concentrated and then diluted with petroleum ether, 0.8 g of a red compound of general formula I, wherein Y=COCH$_3$ and R$_1$=R$_2$=nC$_3$H$_7$, was obtained.

PMR (CDCl$_3$): −0.25 δ[d, CH$_3$(34)]; 0.59 δ[d, CH$_3$(33)]; 0.73 δ[d, CH$_3$(31)]; 0.98 δ[d, CH$_3$(32)]; 1.5–1.66 δ[m, N(CH$_2$CH$_2$CH$_3$)$_2$] 1.78 δ[s, CH$_3$ (13)]; 2.05 δ[s, CH$_3$ (36)]; 2.09 δ[s, CH$_3$(30)]; 2.21 δ[s, CH$_3$(14)]; 3.04 δ[s, OCH$_3$]; 4.91 δ[d, H (25)]; 5.08 δ[dd, H (28)]; 5.80 δ[dd, H (19)]; 6.1–6.8 δ[m, H(17), H(18), H(29)]; 7.78 δ[s, C$\underline{H}$=N—N=CH—N)]; 9.00 δ[s, CH=N—N=C$\underline{H}$—N]; 12.03 and 13.40 δ(s, OH and NH).
MS: 850(M+)

EXAMPLE 7

3-(N-methyl-n-butylaminomethyl-azino)methylrifamycin SV

Following the procedure described in Example 6 and reacting 3-formyl-rifamycin SV hydrazone with chloro-methyl-n-butylformiminium chloride a compound of formula I was obtained, wherein Y=COCH$_3$, R$_1$=CH$_3$, and R$_2$=n—C$_4$H$_9$.

PMR (CDCl$_3$): −0.23 δ[d, CH$_3$(34)]; 0.64 δ[d, CH$_3$(33)]; 0.73 δ[d, CH$_3$(31)]; 0.98 δ[d, CH$_3$ (32)]; 1.44 δ[m,N—CH$_2$CH$_2$CH$_2$CH$_3$]; 1.77 δ[s, CH$_3$(13)]; 2.04 δ[s, CH$_3$ (36)]; 2.07 δ[s, CH$_3$(30)]; 2.14 δ[s, CH$_3$ (14)]; 2.93 δ[s, (N—CH$_3$)]; 3.04 δ[s, OCH$_3$]; 4.7–5.2 δ[m, H (25), H(28)]; 5.5–6.6 δ[m, H(17), H(18), H (29)]; 7.78 δ[s, CH=N—N=CH—N]; 9.01 δ[s, CH=N—N=CH—N]; 12.03 δ[s, NH].
MS: 836 (M+)

EXAMPLE 8

3-(N-di-sec-butylaminomethyl-azino)methylrifamycin SV

Following the procedure described in Example 6 and reacting 3-formyl-rifamycin SV hydrazone with chloro-di-sec-butylformiminium chloride a compound of formula I was obtained, wherein Y=COCH$_3$, R$_1$=R$_2$=sec—C$_4$H$_9$.

PMR (CDCl$_3$): −0.25 δ[d, CH$_3$(34)]; 0.64 δ[d, CH$_3$(33)]; 0.75 δ[d, CH$_3$ (31)]; 1.01 δ[d, CH$_3$(32)]; 1.21 δ[bd, NCHCH$_3$]; 1.55 δ[t, CH$_2$CH$_3$]; 1.78 δ[s, CH$_3$(13)]; 2.05 δ[s, CH$_3$(36)]; 2.09 δ[s, CH$_3$(30)]; 2.22 δ[s, CH$_3$(14)] 3.03 δ[s, OCH$_3$]; 4.20 δ

[m, (N—C$\underline{H}$—)]

4.91 δ[d, H(25)]; 5.10 δ[dd, H(28)]; 5.38 δ[dd, H (19)]; 6.1–6.8 δ[m, H(17), H(18), H(29)]; 7.89 δ[s, C$\underline{H}$=N—N=CH—N]; 8.99 δ[s, CH=N—N=C$\underline{H}$—N]; 11.90; 13.25; 13.82 and 14.01 [s, NH,three OH].
MS: 878 (M+)

EXAMPLE 9

3-(N-methyl-benzylaminomethyl-azino)methylrifamycin SV

Following the procedure described in Example 6 and reacting 3-formyl-rifamycin SV hydrazone with chloro-methyl-benzylformiminium chloride a compound of formula I was obtained, wherein Y=COCH$_3$, R$_1$=CH$_3$, and R$_2$=CH$_2$C$_6$H$_5$.

PMR (CDCl$_3$): −0.23 δ[d, CH$_3$(34)]; 0.64 δ[d, CH$_3$(33)]; 0.72 δ[d, CH$_3$(31)]; 0.96 δ[d, CH$_3$(32)]; 1.77 δ[s, CH$_3$(13)]; 2.04 δ[s, CH$_3$(36)] 2.11 δ[s, CH$_3$(14)]; 2.90 δ[s, NCH$_3$]; 3.02 δ[s, OCH$_3$]; 4.39 δ[bs, CH$_2$C$_6$H$_5$]; 4.7–5.2 δ[m, H(25), H(28)]; 5.5–6.7 δ[m, H(17), H(18), H(29)]; 7.31 δ[m, C$_6$H$_5$]; 7.94 δ[s, C$\underline{H}$=N—N=CH—N]; 9.03 δ[s, CH=N—N=C$\underline{H}$—N]; 12.13 δ[s, NH].
MS: 870 (M+)

EXAMPLE 10

3-(N-diethylaminomethyl-azino)methylrifamycin SV

A solution of 3 g of 3-formyl-rifamycin SV in tetrahydrofuran (150 ml) was added to 0.2 ml of hydrazine hydrate dissolved in tetrahydrofuran (50 ml) cooled at −20° C. After 15' the resulting solution of 3-hydrazonomethyl-rifamycin SV was allowed to reach 0° C., 3 g of chloro-diethylformiminium chloride and 3 ml of triethylamine were added and the reaction was complete within 15'. Ethyl acetate (300 ml) was added, the resulting solution was washed with diluted acetic acid the with water and finally the organic phase was dried over anhydrous sodium sulphate. The solvent was evaporated, the residue was crystallized from ethanol and then from acetone. 1.5 g of a red compound of general formula I was obtained, wherein Y=COCH$_3$, R$_1$=R$_2$=CH$_2$CH$_3$.

PMR (CDCl$_3$): −0.23 δ[d, CH$_3$(34)]; 0.66 δ[d, CH$_3$(33)]; 0.74 δ[d, CH$_3$(31)]; 0.99 δ[d, CH$_3$(32)]; 1.21 δ[t, NCH$_2$C$\underline{H}$$_3$]; 1.79 δ[s, CH$_3$(13)]; 2.06 δ[s, CH$_3$(36)]; 2.10 δ[s, CH$_3$(30)]; 2.23 δ[s, CH$_3$(14)]; 3.04 δ[s, OCH$_3$]; 3.40 δ[m, NC$\underline{H}$$_2$CH$_3$]; 4.91 δ[d, H(25)]; 5.17 δ[m, H(28)]; 5.84 δ[dd, H (19); 6.1–6.6 δ[m, H(29), H(17), H(18)]; 7.77 δ[s, C$\underline{H}$=N—N= CH—N]· 9.05 δ[s,CH=N—N=C$\underline{H}$—N]; 11.95; 13.26; 13.80 and 13.89 δ[s, NH, three OH].
MS: 822 (M+)

EXAMPLE 11

3-(N-pirrolidinomethyl-azino)methylrifamycin SV

Following the procedure described in Example 10 and reacting 3-hydrazonomethyl-rifamycin SV with chloro-pyrrolidinoformiminium chloride a compound of formula I was obtained, wherein Y=COCH$_3$, NR$_1$R$_2$=pyrrolidino.

PMR (CDCl$_3$): −0.27 δ[d, CH$_3$ (34)]; 0.66 δ[d, CH$_3$(33)]; 0.74 δ[d, CH$_3$(31)]; 0.99 δ[d, CH$_3$(32)]; 1.79

δ[s, CH₃(13)]; 1.96 δ[m, N(—CH₂—CH₂—)]; 2.06 δ[s, CH₃(36)]; 2.10 δ[s, CH₃(30)]; 2.23 δ[s, CH₃(14)]; 3.04 δ[s, OCH₃]; 3.45 δ[m, N(CH₂CH₂)₂]; 4.90 δ[d, H(25)]; 5.07 δ[dd, H(28)]; 5.82 δ[dd, H(19)]; 6.1–6.7 δ[m, H(17), H(18), H(29)]; 7.95 δ[s, CH=N—N=CH—N]; 9.08 δ[s,CH=N—N=CH—N]; 11.94; 13.44 and 13.86 δ[s, NH, three OH]
MS: 820 (M+)

Analogously the following compounds of formula I, wherein Y=COCH₃, and R₁ and R₂ have the meaning afterwards specified, were obtained.

$R_1 = R_2 = iC_3H_7$

PMR (CDCl₃): −0.28 δ[d, CH₃(34)]; 0.66 δ[d, CH₃(33)]; 0.76 δ[d, CH₃(31)]; 0.98 δ[d, CH₃(32)]; 1.2–1.3 δ

[m, NCH(CH₃)(CH₃)]

1.78 δ[s, CH₃(13)]; 2.06 δ[s, CH₃(36)]; 2.11 δ[s, CH₃(30)]; 2.22 δ[s, CH₃(14)]; 3.03 δ[s, OCH₃]; 3.45 δ[bd, H(21)]; 3.72 δ[bd, H(27)]; 3.57 δ

[m, NCH(CH₃)(CH₃)];

4.91 δ[d, H(25)]; 5.10 δ[dd, H(28)]; 5.89 δ[dd, H (19)]; 6.28 δ[d, H (29)]; 6.37 δ[d, H(17)]; 6.55 δ[m, H(18)]; 6.89 δ[s, CH=N—N=CH—N]; 9.02 δ[s, CH=N—N=CH—N]; 11.92; 13.28; 13.95 and 14.06 δ[s, NH, three OH].
MS: 850 (M+)

$R_1 = R_2 = nC_4H_9$

PMR (CDCl₃): −0.25 δ[d, CH₃(34)]; 0.66 δ[d, CH₃(33)]; 0.74 δ[d, CH₃(31)]; 1.00 δ[d, CH₃(32)]; 1.3–1.5 δ[m, N(CH₂CH₂CH₂CH₃)₂]; 1.79 δ[s, CH₃(13)]; 2.07 δ[s, CH₃(36)]; 2.11 δ[s, CH₃(30)]; 2.24 δ[s, CH₃(14)]; 3.05 δ[s, OCH₃]; 4.91 δ[d, H(25)]; 5.08 δ[dd, H(28)]; 5.82 δ[dd, H(19)]; 6.1–6.8 δ[m, H(17), H(18), H(29)]; 7.77 δ[s, CH=N—N=CH—N]; 9.03 δ[s, CH=N—N=CH—N] 11.97; 13.28; 13.81 and 13.93 δ[s, NH, three OH]
MS: 878 (M+)

$R_1 = CH_3, R_2 = C_6H_5$

PMR (CDCl₃): −0.28 δ[d, CH₃(34)]; 0.58 δ[d, CH₃(33)]; 0.66 δ[d, CH₃(31)]; 0.95 δ[d, CH₃(32)]; 1.80 δ[s, CH₃(13)] 2.06 δ[s, CH₃(36)]; 2.11 δ[s, CH₃(30)]; 2.23 δ[s, CH₃(14)]; 3.04 δ[s, OCH₃]; 3.43 δ[s, NCH₃]; 3.77 δ[bd, H(27)]; 4.95 δ[bd, H(25)]; 5.14 δ[dd,H(28)]; 5.74 δ[dd, H(19)]; 6.26 δ[d, H(29)]; 6.34 δ[d, H(17)]; 6.59 δ[bdd, H(18)]; 7.1–7.5 δ[m, NC₆H₅]; 8.37 δ[s, CH=N—N=CH—N]; 9.17 δ[s, CH=N—N=CH—N]; 12.07; 13.25; 13.78 and 13.87 δ[s, NH, three OH].
MS: 856 (M+)

$R_1 = CH_3, R_2 = C_6H_{11}$

MS = 862 (M+)
Rf = 0.38 in CH₂Cl₂: MeOH 20:1

In a similar manner the following compounds of formula (I) were obtained, only the meanings of the radicals R₁ and R₂ being here specified $R_1 = CH_3CH_3, R_2 = CH_2CH_2OH$ $R_1 = CH_2CH_3, R_2 = CH_2CH_2OCH_3$ and R₁ and R₂ together with the N atom to which they are bounded form a 4-substituted-1-piperazinyl group in which the substituent in position 4 is CH₃, i—C₄H₉ or cyclopentyl group.

The activity in vitro of the rifamycin compounds obtained as described in Examples 1, 2 and 3 have been tested against some Gram-positive and Gram-negative microorganisms and against Mycobacterium Tuberculosis (serial dilution method).

The results are set out in the following Table, wherein the novel compounds are compared with Rifampicin and the figures are the values of the minimal inhibiting concentrations (MIC) given in mcg/ml.

TABLE

| Microorganisms | Example 1 | Example 2 | Example 3 | Rifampicin |
|---|---|---|---|---|
| K. Pneumoniae | 10 | 20 | 20 | 10 |
| P. vulgaris | 10 | 20 | 10 | 10 |
| E. coli B | 10 | 20 | 10 | 10 |
| E. coli ginetta | 10 | 20 | 10 | 10 |
| E. coli ClRifR | >200 | 200 | 200 | >200 |
| P. aeruginosa | 5 | 20 | 10 | 10 |
| S. abortivoequina | 5 | 20 | 10 | 10 |
| S. aureus 209 P | 0.037 | 0.009 | 0.018 | 0.018 |
| S. foecalis | 0.6 | 0.6 | 0.6 | 0.6 |
| S. pyogenes | 1.25 | 1.25 | 2.5 | 2.5 |
| S. lutea | 0.037 | 0.018 | 0.037 | 0.037 |
| S. aureus 209 P Rif R | >200 | >200 | >200 | >200 |
| M. tuberculosis H37Rv | 0.01 | 0.02 | 0.02 | 0.01 |

What we claim is:
1. A rifamycin having the formula (I)

[Chemical structure of rifamycin formula (I) showing CH=N—N=CH—NR₁R₂ substituent]

wherein Y is a hydrogen atom or an acetyl group; R₁ is a linear or branched alkyl group having about 1 to 7 carbon atoms or an alkenyl group having about 3 or 4 carbon atoms; R₂ is a linear or branched alkyl group having about 1 to 7 carbon atoms a chloroalkyl group having about 2 to 4 carbon atoms, an alkenyl group having about 3 or 4 carbon atoms, a cycloalkyl group having about 3 to 7 carbon atoms in the ring, a cycloalkyl alkyl group having about 3 to 6 carbon atoms in the ring, a phenyl group, an unsubstituted aralkyl group having about 7 or 8 carbon atoms or an aralkyl group having about 7 or 8 carbon atoms being substituted by 1 halogen atom in the aryl group; or R₁ and R₂ along with the nitrogen atom to which they are bonded form a cyclic moiety, said moiety being pyrrolidinyl, piperidinyl, hexahydroazepinyl or heptahydroazocinyl, each of which are unsubstituted or substituted with 1 or 2 methyl radicals, 4-alkyl-1-piperazinyl, morpholinyl or 1, 2, 3, 4-tetrahydroisoquinolinyl.

2. A rifamycin having a formula (II)

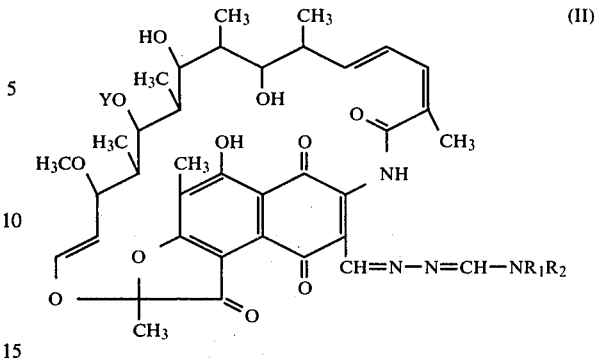

wherein Y, $R_1$ and $R_2$ are as defined in claim 1.

3. An antibacterial preparation which comprises the antibacterial composition of claim 2, in unit dosage form.

4. An antibacterial composition which comprises a rifamycin compound as claimed in claim 1 or 2, and a pharmaceutically acceptable carrier or diluent therefor.

5. An antibacterial preparation which comprises a rifamycin compound as claimed in claim 1 or 2, in unit dosage form.

* * * * *